United States Patent [19]

Thorogood et al.

[11] Patent Number: 4,562,199

[45] Date of Patent: Dec. 31, 1985

[54] IMIDAZOLE DERIVATIVES, COMPOSITIONS AND USE

[76] Inventors: Peter B. Thorogood, 2 Lansdowne Gardens, London, S.W.8.; Jeremy G. Vinter, Bailay's Glen, Weston, Hitchin, Herts, both of England

[21] Appl. No.: 522,228

[22] Filed: Aug. 11, 1983

[51] Int. Cl.$^4$ .................. A61K 31/415; C07D 233/60
[52] U.S. Cl. ..................................... 514/399; 548/335
[58] Field of Search ................... 548/335; 424/273 R; 514/399

[56] References Cited

U.S. PATENT DOCUMENTS 4,226,878 10/1980 Iizuka et al. .................. 548/335
4,431,815 2/1984 Thorogood .................. 548/335

Primary Examiner—Robert W. Ramsuer
Attorney, Agent, or Firm—Donald Brown

[57] ABSTRACT

Compounds of the formula:

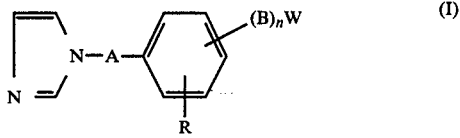

wherein R is $(Hal)_m$ wherein Hal represents a halogen atom and m is 1 or 2, or R is-$(B^1)_{n^1}W^1$ wherein $B^1$, $n^1$ and $W^1$ are as defined below;

W and (when present) $W^1$, which may be the same or different, each represents a carboxyl, esterified carboxyl, amide, N-$C_{1-4}$ alkyl-amide, N,N-di-($C_{1-4}$ alkyl)-amide, nitrile, aldehyde, amino, hydroxymethyl, or tetrazolyl group;

n and (when present) $n^1$ which may be the same or different, are each 0 or 1; and A, B and (when present) $B^1$, which may be the same or different, each represents a straight chain or branched $C_{1-3}$ alkylene or $C_{2-3}$ alkenylene group.

These compounds have been found to possess potent and selective inhibitory activity against thromboxane synthetase which renders the compounds useful in the treatment or prophylaxis of thrombo-embolic disorders.

19 Claims, No Drawings

IMIDAZOLE DERIVATIVES, COMPOSITIONS AND USE

The present invention relates to imidazole derivatives and salts thereof, their synthesis, pharmaceutical formulations containing such compounds and the use of these compounds in medicine.

Thromboxane $A_2$ ($TXA_2$), a potent stimulator of blood platelet aggregation, is produced in platelets from the prostaglandin endoperoxides $PGG_2$ and $PGH_2$. Prostacyclin ($PGI_2$), which has potent anti-aggregatory activity, is also produced (in blood vessel walls) from $PGG_2$ and $PGH_2$ and it has been suggested that a balance between the production of $TXA_2$ and $PGI_2$ is the controlling factor in thrombus formation. It would, in consequence, be desirable in the treatment or prophylaxis of thrombo-embolic disorders to be able selectively to inhibit $TXA_2$ synthetase, thereby favouring the production of the anti-aggregatory agent $PGI_2$.

Imidazole derivatives substituted in the 1-position by a very wide variety of differing organic groupings, including aliphatic, aryl, araliphatic and heterocyclic groups have been proposed for use as thromboxane synthetase inhibitors, for example, as described in UK Patent Specifications Nos. 2008089A, 2006752A, 2010813A, 2018136A and 2044259A. In order to ensure an optimum therapeutic effect, it is desirable for $TXA_2$ synthetase inhibitors to have high potency and/or a high selectivity, i.e. a pharmacological action whereby $TXA_2$ synthetase is inhibited whereas $PGI_2$ synthetase (responsible for the formation of $PGI_2$) is relatively unaffected. A prolonged duration of action is also desirable.

We have now discovered that the 1-substituted imidazoles of formula (I) below and their physiologically acceptable salts (hereinafter referred to as the "active compounds") have advantageous $TXA_2$ synthetase inhibitory activity.

The compounds of formula (I) are those of formula

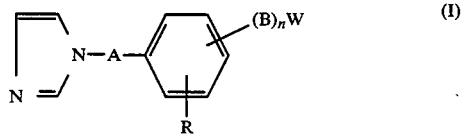

wherein R is $(Hal)_m$ wherein Hal represents a halogen atom and m is 1 or 2, or R is $-(B^1)_{n^1}W^1$ wherein $B^1$, $n^1$ and $W^1$ are as defined below;

W and (when present) $W^1$, which may be the same or different, each represents a carboxyl, esterified carboxyl, amide, $N-C_{1-4}$ alkyl-amide, $N,N$-di-($C_{1-4}$ alkyl)-amide, nitrile, aldehyde, amino, hydroxymethyl, or tetrazolyl group;

n and (when present) $n^1$ which may be the same or different, are each 0 or 1; and A, B and (when present) $B^1$, which may be the same or different, each represents a straight chain or branched $C_{1-3}$ alkylene or $C_{2-3}$ alkenylene group.

In formula (I) above, A advantageously represents a straight chain $C_{1-3}$ alkylene group, e.g. a methylene or ethylene group; or a group of formula $-CH=CH-$; n is preferably 1; and Hal is selected from fluorine, chlorine, bromine or iodine, preferably chlorine or bromine, while W and (when present) $W^1$ preferably each represent a carboxyl group. It should be noted that in formula (I), the $-Hal$ and R substituents may be present in any desired position on the phenyl ring. However, the R substituent is advantageously present in the 2-position while the $(B)_nW$ substituent is preferably present in the 4-position of the phenyl ring. Especially preferred compounds include those wherein n is 1 and B is a group of formula $-CH=CH-$ and W and (when present) $W^1$ each represent a carboxyl group.

Particularly preferred compounds of formula (I) include
3-[3-chloro-4-(imidazol-1-ylmethyl)phenyl]-prop-2-enoic acid and its ethyl ester, and
3-[3-bromo-4-(imidazol-1-ylmethyl)phenyl]-prop-2-enoic acid and its ethyl ester.

The above compounds of formula (I) have been found to have a high inhibitory activity in vitro against $TXA_2$ synthetase coupled with a high selectivity and a prolonged duration of action in vivo.

Physiologically acceptable salts of compounds of formula (I) include base salts e.g. alkali metal such as sodium or potassium or alkaline earth metal such as calcium salts, and acid addition salts, e.g. salts derived from the following acids: oxalic, hydrochloric, hydrobromic, sulphuric, nitric, perchloric, fumaric, maleic, phosphoric, glycollic, lactic, salicyclic, succinic, toluene-p-sulphonic, tartaric, acetic, citric, methanesulphonic, formic, benzoic, malonic, naphthalene-2-sulphonic and benzenesulphonic acids.

The present invention also includes within its scope pharmaceutically acceptable bioprecursors (otherwise known as pro-drugs) of the compounds of formula (I), i.e. compounds which have a different formula to formula (I) above but which nevertheless upon administration to an animal or human being are converted directly or indirectly in vivo into a compound of formula (I).

When the compounds of formula (I) contain an asymmetric centre, the present invention includes the optically active stereoisomers as well as racemic mixtures thereof. If desired, the optically active stereoisomers may be resolved in conventional manner, e.g. by fractional crystallisation of the diastereoisomeric salts. Geometrical isomers of compounds of formula (I) are also included.

Imidazoles of formula (I) and acid addition salts thereof may be prepared in conventional manner using techniques known in the art for the synthesis of compounds of analogous structure.

According to a further feature of the present invention we provide a process for the preparation of compounds of formula (I) (as defined in claim 1) and their physiologically acceptable salts which comprises (a) reacting imidazole or a salt thereof with a compound of formula

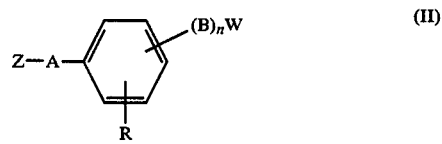

(wherein A, B, n, R and W are as defined above and Z is a leaving group);

(b) reacting a compound of

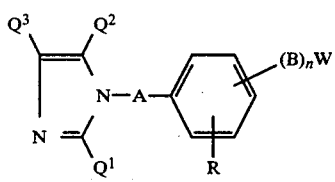 (III)

(wherein A, B, n, R and W are as defined above and $Q^1$, $Q^2$ and $Q^3$ are the same or different, at least one being a radical capable of selective removal, the remainder being selected from hydrogen and radicals capable of removal in the same or a different manner to the first-mentioned radical) under conditions to remove the said radical(s).

(c) conversion of a compound of formula

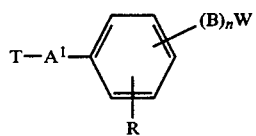 (IV)

wherein R, B, n and W are as hereinbefore defined, T is 1-imidazoline, 1-pyrazole or 1-imidazole group and $A^1$ is a straight or branched chain $C_{2-3}$ alkylene group containing an oxo group or (providing T is a 1-imidazoline or 1-pyrazole group) $A^1$ is as defined for A above.

(d) oxidation of a compound of formula

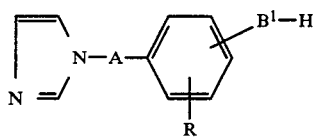 (V)

(wherein A and R are as hereinbefore defined and $B^1$ is a $C_{1-4}$ alkylene group or a $C_{2-4}$ alkenylene group) to form a corresponding compound of formula (I) wherein n is 1, B is as herebefore defined and W represents a carboxyl group.

(e) reaction of a compound of formula

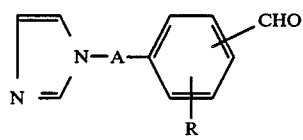 (VI)

(wherein A and R are as hereinbefore defined) with an appropriate Wittig reagent to form a corresponding compound of formula (I) wherein n is 1 and B is a $C_{2-3}$ alkenylene group.

(f) reaction of a compound of formula

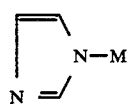 (VII)

(wherein M is a $C_{2-3}$ alkenyl group) with a compound of formula

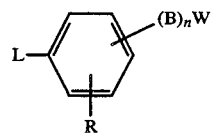 (VIII)

(wherein R, B, n and W are as defined above and L represents a group cabable of reacting with the group M in formula (VII), e.g. a bromine or iodine atom) to form a corresponding compound of formula (I) wherein A is a $C_{2-3}$ alkenylene group) and optionally effecting one or more of the following conversions in any desired order:

(i) when at least one of A, B and $B^1$ represents a $C_{2-3}$ alkenylene group, converting the said group to a $C_{2-3}$ alkylene group.

(ii) when at least one of W and $W^1$ represents a group as specified above other than a carboxyl group, converting the said group to a carboxyl group.

(iii) when at least one of W and $W^1$ represents a carboxyl or esterified carboxyl group, converting the said group to an amide, N—$C_{1-4}$ alkyl-amide or N,N—di—$C_{1-4}$ alkyl-amide group.

(iv) when at least one of W and $W^1$ represents a carboxyl group, converting the said group to an esterified carboxyl or carboxylate salt group.

(v) when at least one of W and $W^1$ represents a nitrile group, converting the said group to a tetrazolyl group.

Process (a) above involves the reaction of imidazole or a salt thereof e.g. an alkali metal such as sodium, or a silver salt, with a compound of formula (II). This reaction is well established in the literature, and the leaving group may be chosen from a variety of substituents, especially halo, preferably chloro or bromo, arylsulphonyloxy, preferably p-toluene-sulphonyloxy, alkanesulphonyloxy or arylalkylsulphonyloxy radicals. Alternatively, Z may represent a trialkylammonium cation, e.g. a trimethylammonium cation, in association with an appropriate anion. The reaction is preferably performed in the presence of an acid acceptor, for example, an alkali metal alkoxide, such as sodium methoxide or potassium tertiary butoxide, generally in a solvent medium, for example an alkanol or N,N-dimethyl formamide. In some cases it may be advantageous to perform the reaction in the presence of a crown ether e.g. 18-crown-6, preferably in an ether solvent. When Z is halo, the reaction may be carried out in the presence of a copper catalyst, e.g. as in an Ullmann reaction. The leaving group Z may itself be formed in situ from the corresponding alkanol (Z=OH) by reaction with a hydrohalogenic acid (e.g. hydrochloric acid or a Lewis acid, such as aluminum chloride: see Japanese Patent Kokai No. 131577/77) and the resulting agent of formula (III) reacted directly with imidazole without prior isolation.

Alternatively an alkanol (Z=OH) may be reacted directly with imidazole by heating in the presence of a dehydrating agent such as phosphoric acid, or a phosphate (see Japanese Patent Publication No. 51 105 060), sulphuric acid or sulphates (see Japanese Patent Publication No. 51 105 061).

In process (b), the symbols $Q^1$, $Q^2$ and $Q^3$ may be removable by, for example, reduction or oxidation and selected for example from thio (—SH), $C_{1-4}$-alkyl-thio or halo, preferably chloro or bromo. The reaction conditions are chosen according to the nature of the radicals $Q^1$, $Q^2$ and $Q^3$. Desulphurisation may be performed by oxidative or reductive procedures using, for example, nitric acid or Raney nickel; and reductive dehalogenation by the use of zinc and acetic acid or Raney nickel or other reagents known in the art or described in the literature.

In process (c), for example, an imidazoline of formula

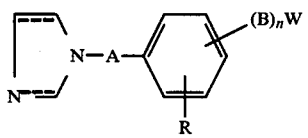
(IX)

wherein one of ---------- represents an extra bond, and A, B, n and Hal are as defined in formula (I) may be dehydrogenated to the corresponding imidazole in the presence of a catalyst, for example by heating to 250° C. in the presence of palladium, nickel or platinum under pressure, or by heating with a dehydrogenating agent, such as selenium or copper oxide. 1-Pyrazole compounds may be treated with ultra-violet radiation, optionally under an inert atmosphere (e.g. argon) in for example 1,2-dimethoxyethane at room or elevated temperature (see for example "Ring Transformations of Heterocycles" edited van der Plas, Academic Press, 1973 at page 261).

Alternatively, in process (c) for example, a compound of formula

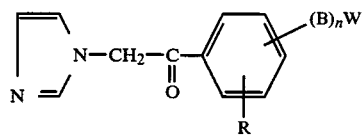
(X)

where B, n, W and R are is as defined in formula (I), may be reduced at the keto group to a —CH$_2$— group, for example by a Clemmensen reduction.

With regard to process (d), the oxidation may be effected, for example, by the use of potassium permanganate, advantageously in benzene, or by sodium hypochlorite, advantageously in acetonitrile.

With regard to process (e), the reaction may be carried out using, for example, a Wittig reagent of formula

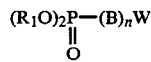

(wherein $R_1$ is a $C_{1-4}$ alkyl group, n is 1, B is a alkylene group and W is as herebefore defined). Other alternative Witting reagents may be employed including those described for example in Principles of Organic Synthesis, Ed. R. O. C. Norman (2nd Ed), J. Wiley & Sons, page 484.

With regard to process (f), the reaction is advantageously effected in the presence of a transition metal catalyst such as palladium, or a complex thereof with an arylphosphine such as triphenylphosphine, preferably in the presence of a base, e.g. triethylamine or tri-n-butylamine. Reaction under superatmospheric pressure may be advantageous.

In optional step (i) above, the conversion may be effected for example by catalytic hydrogenation, preferably in the presence of a transition metal catalyst, e.g. palladium.

(ii) Compounds of formula (I) where at least one of W and $W^1$ represents a carboxyl group may be prepared by hydrolysis of a corresponding compound of formula (I) wherein at least one of W and $W^1$ represents an ester or nitrile group. The hydrolysis may be effected for example, in an acidic medium, for example, in the presence of HCl or in a basic medium, for example, in the presence of sodium hydroxide.

With regard to optional step (iii) above, this may be effected for example by treatment of the parent compound with an appropriate amine.

Compounds of formula (I) wherein at least one of W and $W^1$ represents a tetrazolyl group may be prepared, for example, from a corresponding nitrile compound by reaction with an azide, eg, sodium azide in the presence of ammonium chloride.

The intermediates for use in the above described reactions may also be made by conventional methods known in the art.

The physiologically acceptable acid addition salts of the compounds of formula (I) may be prepared by any method known in the art. In particular they may be prepared by treating the parent imidazole with the appropriate acid or by anion-exchange.

The imidazoles of formula (I) may be used in conjunction with a phosphodiesterase inhibitor, for example, theophylline or dipyridamole, which provides a further synergistic increase in effect, as it acts against platelet aggregation by a different pathway.

The active compounds are particularly useful in the treatment and/or prophylaxis of thrombo-embolic disorders in mammals, including man. It is to be understood that the term "thrombo-embolic disorders" includes those disorders whose etiology is associated with platelet aggregation.

According to a further feature of the present invention we therefore provide an active compound (as defined above) for use in the treatment or prophylaxis of thrombo-embolic disorders in a mammal, e.g. man.

The active compounds are useful wherever it is desired to inhibit platelet aggregation and/or to reduce the adhesive character of platelets, and consequently to treat or prevent the formation of thrombi in mammals, including man. For example, the compounds are useful in the treatment and prevention of myocardial infarcts, cerebro-vascular thrombosis and ischaemic peripheral vascular disease; to treat and prevent post-operative thrombosis; and to promote patency of fascular grafts following surgery.

The active compounds are also useful as an addition to blood, blood products blood substitutes, and other fluids which are used in artifical extra-corporeal circulation and perfusion of isolated body portions, e.g. limbs and organs, whether attached to the original body, detached and being preserved or prepared for transplant, or attached to a new body. They may also be used in laboratory animals, e.g. cats, dogs, rabbits, monkeys and rats, for these purposes, in order to develop new methods and techniques for organ and limb transplants.

The active compounds may also exhibit some vasodilatory action on blood vessels and therefore have a utility as anti-hypertensives for the treatment of high blood pressure in mammals, including man.

The active compounds may also be used in the prevention, treatment or prophylaxis of angina pectoris and in the prevention or delay of the onset of shock. The active compounds may also be used in the treatment of migraine or asthma.

The amount of active compound required for therapeutic or prophylactic effect will vary with the route of administration, and the nature of the condition under treatment. In general a suitable dose for a mammal, including man, of active compound will lie in the range of 0.1 to 300 mg per kg body weight, particularly from 0.5 to 10 mg per kg body weight, for example 8 mg per kg. A suitable single oral dose for an adult human lies within the range of 50 to 1800 mg, preferably 200 to 900 mg, especially 300 to 700 mg, for example 550 mg, given say three times a day.

While it is possible for an active compound to be administered per se, it is preferable to present it as a pharmaceutical formulation. The formulation, both for veterinary and for human medical use, of the present invention comprise an active compound as above defined, together with one or more acceptable carriers therefor and optionally other therapeutic ingredients. The carrier(s) must be 'acceptable' in the sense of being compatible with the other ingredients of the formation and not being deleterious to the recipient thereof. Unit doses of a formulation may contain between 60 mg and 1.5 g of an active compound.

The formulations include those suitable for oral, rectal, vaginal or parenteral (including subcutaneous, intramuscular and intavenous) administration. Preferred formulations include tablets, capsules, elixirs and injectable suspensions or solutions.

The formulations may conveniently be presented in unit dosage form and may be prepared in conventional manner, e.g. by bringing into association the active compounds (in the form of the base or a physiologically acceptable salt) with the carrier which may comprise one or more accessary ingredients. In general the formulations are prepared by uniformly and intimately bringing into association the active compound with liquid carriers or finely divided solid carriers or both, and then, if necessary, shaping the product into the desired formulation.

The following Examples illustrate the present invention. All temperatures are given in degrees Celsius.

EXAMPLE 1

1-(4-Carboxy-2-chlorobenzyl)imidazole (a) 4-Bromomethyl-3-chlorobenzonitrile

A mixture of 3chloro-4-methylbenzonitrile (5.0 g, 0.033 mol), N-bromosuccinimide (5.87 g, 0.033 mol) and 2,2'-azobis(2-methylpropionitrile) (0.08 g) in dry carbon tetrachloride (40 ml) was stirred and irradiated with a tungsten lamp for 2 h, during which time the reaction mixture refluxed steadily.

The reaction mixture was filtered hot and the filtrate was concentrated under reduced pressure, giving a brown oil which solidified on cooling. Recrystallisation of the solid from petroleum ether (b.p. 40°–60° C.)/ether afforded 4-bromomethyl-3-chlorobenzonitrile as a yellow crystalline solid, m.p. 80°–83°.

(b) 1-(2-Chloro-4-cyanobenzyl)imidazole

Imidazole (0.08 g, 1.18 mmol) was added to a stirred mixture of 1,4,7,10,13,16-hexaoxacyclooctadecane (18-crown-6; 0.04 g, 0.15 mmol) and potassium tert-butoxide (0.15 g, 1.34 mmol) in dry ether (5 ml). After stirring this mixture for 0.33 h, 4-bromomethyl-3-chlorobenzonitrile (0.03 g, 1.3 mmol) in dry ether (5 ml) was added dropwise. Following the addition, the reaction mixture was stirred for 3 h at ambient temperature, and then set aside overnight.

Next day, water (8 ml) was added to the reaction mixture, and the organic phase was separated. The aqueous layer was extracted with ether (3×15 ml), and the organic solutions were combined, washed with saturated brine (10 ml) and then dried (MgSO$_4$), to give a brown solid. The solid was purified using a silica gel column and by elution with chloroform/methanol (9:1). Concentration of the product fractions afforded the product as a pale yellow solid.

(c) 1-(4-Carboxy-2-chlorobenzyl)imidazole hydrochloride

A mixture of 1-(2-chloro-4-cyanobenzyl)imidazole (0.2 g, 0.92 mmol) and hydrochloric acid (6M, 3 ml) was stirred and boiled for 3 h. After cooling, the reaction mixture was concentrated under reduced pressure to afford a white solid.

After the addition of ethanol (10 ml) to the solid, and concentration under reduced pressure (this procedure was repeated three times) the resulting solid as recrystallised from ethyl acetate/petroleum ether (b.p. 40°–60°), giving 1-(4-carboxy-2-chlorobenzyl)imidazole hydrochloride as white plates, m.p. 265°–269°.

EXAMPLE 2

Ethyl 3-/3-chloro-4-(imidazol-1-ylmethyl)phenyl/-prop-2-enoate (a) Cuprous Cyanide A mechanically stirred solution of cupric sulphate pentahydrate (1080.0 g, 4.33 mol) in water (3000 ml) was heated to 60° when hydrochloric acid (2M) was added dropwise until the solution was acid to Congo Red. A solution of sodium metabisulphite (276.15 g, 1.453 mol) in water (870 ml) was then added to the copper sulphate solution at 50°–60°. A solution of potassium cyanide (302.4 g, 4.64 mol) in water (870 ml) was then heated to 60° and added to the vigorously stirred reaction mixture.

Following the addition, the reaction mixture was stirred at 60° C. for 0.5 h, filtered and the residue was washed well with hot water.

(b) 3-Chloro-4-methylbenzonitrile

A mixture of 3-chloro-4-methylaniline (515.01 g, 3.64 mol), concentrated hydrochloric acid (930 ml) and water (930 ml) was stirred and cooled to 0°, when a solution of sodium nitrite (259.77 g, 3.765 mol) in water (540 ml) was added dropwise at 0°–5°.

The cuprous cyanide prepared in (a) was then dissolved in sodium cyanide solution [sodium cyanide (421.98 g, 8.6 mol) in water 1350 ml], and this solution was heated to 70° when the cold diazonium salt solution was added dropwise to the rapidly stirred cuprous cyanide solution at 60°–70°. Following the addition, the reaction mixture was stirred at 70° for 0.5 h.

Ether (3000 ml) was then added to the reaction mixture, and this mixture was then filtered. The ether layer was separated, and was then washed with hydrochloric acid (1500 ml, 2M), and then with water (1500 ml). The ether solution was then dried (MgSO$_4$) and concentrated under reduced pressure to afford a dark brown solid. Distillation of the solid in vacuo afforded 3-chloro-4-methylbenzonitrile as a yellow solid, b.p. 120°–126°/16 mmHg. Recrystallisation of the solid from aqueous ethanol gave the product as a fine white crystalline solid, m.p. 46.5°–47.5°.

(c) 3-Chloro-4-methylbenzaldehyde

A mixture of 3-chloro-4-methylbenzonitrile (4.0 g, 26.39 mmol), formic acid (72 ml, 75% v/v) and nickel aluminum alloy (50/50, 4.8 g) was stirred and heated under reflux for 2 h. The reaction mixture was then filtered hot through Hyflo, and the residue was washed well with hot ethanol. The filtrate was concentrated under reduced pressure to yield a sticky solid. Distillation of this solid afforded 3-chloro-4-methylbenzaldehyde as a colourless oil, b.p. 73°–74°/0.8 mmHg.

(d) Ethyl 3-(3-chloro-4-methylphenyl)prop-2-enoate

A stirred mixture of sodium hydride (50% dispersion in oil; 0.93 g, 19.35 mmol) in dry 1,2-dimethoxyethane (30 ml) under dry nitrogen was treated dropwise at ambient temperature with a solution of triethyl phosphonoacetate (4.35 g, 19.4 mmol) in dry 1,2-dimethoxyethane (10 ml). Following the addition, the reaction mixture was stirred at room temperature for 1 h.

A solution of 3-chloro-4-methylbenzaldehyde (3.0 g, 19.41 mmol) in dry 1,2-dimethoxyethane (10 ml) was then added dropwise, and the reaction mixture was then stirred at ambient temperature for 1.5 h.

The reaction mixture was poured into ice/water (50 ml), the resulting oil was separated, and the aqueous solution was extracted with ethyl acetate (3×50 ml), and the organic solutions were combined and dried ($MgSO_4$). Concentration of the organic solution under reduced pressure afforded a brown oil, which was distilled, to give ethyl 3-(3-chloro-4-methylphenyl)prop-2-enoate as a colourless oil, b.p. 98°–104°/0.5 mmHg.

(e) Ethyl 3-(4-bromomethyl-3-chlorophenyl)prop-2-enoate

A mixture of ethyl 3-(3-chloro-4-methylphenyl)-prop-2-enoate (10.0 g, 44.5 mmol), N-bromosuccinimide (31.7 g, 178.1 mmol) and 2,2′-azo-bis-(2-methylpropionitrile) (0.1 g) in dry carbon tetrachloride (100 ml) was stirred and irradiated with a tungsten lamp for 5 h, during which time the mixture refluxed gently. After this time, a further quantity of 2,2′-azo-bis-(2-methylpropionitrile) (1.0 g) was added and the mixture was irradiated with the tungsten light for a further 6.5 h. The reaction mixture was filtered hot, and the filtrate was concentrated under reduced pressure to afford a dark brown oil (25.7 g).

The oil was purified using a silica gel column, and by elution with petroleum ether/chloroform (7:3), giving ethyl 3-(4-bromomethyl-3-chlorophenyl)-prop-2-enoate as a colourless solid, m.p. 263°–265° C.

(f) Ethyl (E)-3-[3-chloro-4-(imidazol-1-ylmethyl)-phenyl]prop-2-enoate

Imidazole (0.078 g, 1.14 mol) was added to a stirred solution of 18-crown-6 (0.03 g, 1.14 mmol) and potassium t-butoxide (0.15 g, 1.34 mmol) in dry ether (5.0 ml). The reaction mixture was then stirred at room temperature for 1.0 h. Ethyl (E)-3-(4-bromomethyl-3-chlorophenyl)prop-2-enoate (0.4 g, 1.32 mmol) in dry ether (3.0 ml) was then added dropwise to the stirred reaction mixture, and the reaction mixture was then stirred overnight at room temperature.

Water (4.0 ml) was then added, the organic layer was separated, and the aqueous layer was extracted with ether (3×5 ml). The organic solutions were combined, washed with saturated brine (10 ml) and dried ($MgSO_4$). Concentration of the organic solution afforded a yellow crystalline solid, which was recrystallised from aqueous ethanol, to afford the product as a pale yellow solid, m.p. 112°–114°.

EXAMPLE 3

(E)-3-[3-Chloro-4-(imidazol-1-ylmethyl)phenyl]prop-2-enoic acid hydrochloride

A mixture of ethyl (E)-3-[3-chloro-4-(imidazol-1-ylmethyl)phenyl]prop-2-enoate (0.1 g, 0.31 mmol) and hydrochloric acid (6M, 2.0 ml) was stirred and boiled for 2 h. The reaction mixture was then concentrated under reduced pressure, when ethanol (4.0 ml) was added and the reaction mixture was again concentrated.

The procedure was repeated four times, giving a white solid. Recrystallisation of the solid from ethanol/petroleum ether (b.p. 40°–60°) gave (E)-3-[3-chloro-(4-imidazol-1-ylmethyl)phenyl]prop-2-enoic acid hydrochloride as a white solid, m.p. 218°–220°.

EXAMPLE 4

3-[3-Chloro-4-(imidazol-1-ylmethyl)phenyl]propanoic acid hydrochloride

A mixture of (E)-3-[3-chloro-4-(imidazol-1-ylmethyl)phenyl]prop-2-enoic acid hydrochloride (0.07 g) and 5% palladium on barium sulphate (0.01 g) in ethanol was stirred under an atmosphere of hydrogen until the theoretical amount of hydrogen had been consumed. The catalyst was then filtered off (Hyflo) and the reaction mixture was concentrated to afford a colourless oil. N.M.R. spectroscopy of the product showed that it was consistent with the proposed structure.

Example 5

Ethyl 3-[3-bromo-4-(imidazol-1-ylmethyl)phenyl]prop-2-enoate (a) 3-Bromo-4-methylbenzaldehyde.

This compound was prepared according to the method of Eizember and Ammons, Organic Preparations and Procedures Int. 1974, 6(5), 251. The product was obtained as a beige crystalline solid, m.p. 47°–49°.

(b) Ethyl 3-(3-bromo-4-methylphenyl)prop-2-enoate.

To a stirred mixture of sodium hydride (50% dispersion in oil; 10.84 g, 0.226 mol) in dry 1,2-dimethoxyethane (240 ml) under dry nitrogen was added drop-wise triethyl phosphonoacetate (50.6 g, 0.226 mmol) in dry 1,2-dimethoxyethane (60 ml). Following the addition, the reaction mixture was stirred at ambient temperature for 1 h. A solution of 3-bromo-4-methylbenzaldehyde (45.0 g, 0.226 mol) in dry 1,2-dimethoxyethane (60 ml) was then added dropwise over 1.5 hours, and the reaction mixture was then stirred at ambient temperature overnight.

Next day, the reaction mixture was stirred and heated under reflux for 1.5 h and was then cooled. The reaction was poured onto a stirred ice/water mixture, and the resulting oil was extracted with ethyl acetate (3×300 ml). The ethyl acetate extracts were combined dried ($MgSO_4$) and then concentrated to afford a yellow oil. Distillation of the oil afforded ethyl 3-(3-bromo-4-methylphenyl)prop-2-enoate as a white solid, b.p. 124°–126°/0.15 mm Hg.

(c) Ethyl 3-(3-bromo-4-bromomethylphenyl)prop-2-enoate

A mixture of ethyl 3-(3-bromo-4-methylphenyl)prop-2-enoate (4.0 g, 0.015 mol), N-bromosuccinimide (5.34 g, 0.03 mol) and 2,2'-azobis-(2-methylpropionitrile) (0.2 g) in dry carbon tetrachloride (25 ml) was stirred and irradiated with a tungsten lamp for 14 h and was then set aside at ambient temperature overnight. Next day the reaction mixture was reheated to boiling, filtered hot, and the filtrate was concentrated under reduced pressure to afford a brown oil.

The oil was purified by 'flash' chromatography, using chloroform/methanol 9:1 as eluant, to give ethyl 3-(3-bromo-4-bromomethylphenyl)prop-2-enoate as a white solid.

(d) A mixture of imidazole (0.25 g, 3.67 mmol), potassium tert-butoxide (0.42 g, 3.75 mmol), ethyl 3-(3-bromo-4-bromomethylphenyl)prop-2-enoate (1.29 g, 3.7 mmol) and 18-crown-6 (0.1 g) in dry ether was stirred at room temperature for 72 h. Water (5 ml) was then added, and the aqueous layer was extracted with ether (3×50 ml). The ether solutions were combined, dried (MgSO$_4$) and then concentrated to afford a pale yellow oil. The oil was 'flash' chromatographed using chloroform/methanol 9:1 as eluant. The product fractions were combined, dried (MgSO$_4$) and concentrated to afford ethyl 3-[3-bromo-4-(imidazol-1-ylmethyl)-phenyl]prop-2-enoate as a white solid. NMR data was consistent with the assigned structure.

EXAMPLE 6

3-[3-Bromo-4-(imidazol-1-ylmethyl)phenyl]prop-2-enoic acid hydrochloride hydrate A mixture of ethyl 3-[3-bromo-4-(imidazol-1-ylmethyl)phenyl]prop-2-enoate (0.12 g) in hydrochloric acid (2 ml, 6M) was stirred and heated under reflux for 2 h. The reaction mixture was concentrated under reduced pressure and toluene (5 ml) was added and the reaction mixture was again concentrated to give a white solid. Recrystallisation of the solid from ethanol/ether gave 3-[3-bromo-4-(imidazol-1-ylmethyl)phenyl]prop-2-enoic acid hydrochloride as a white solid, m.p. 247°–249°.

EXAMPLE 7

Ethyl 3-[3-cyano-4-(imidazol-1-ylmethyl)phenyl]prop-2-enoate

A mixture of ethyl 3-[3-bromo-4-(imidazol-1-ylmethyl)phenyl]prop-2-enoate (0.2 g) and cuprous cyanide (0.07 g) in dry N,N-dimethylformamide (1 ml) was stirred and heated under reflux for 8 h. The hot reaction mixture was poured into a stirred solution of 1,2-diaminoethane (0.3 ml) and water (1.5 ml). The reaction mixture was filtered, and the residue was washed with hot benzene 2×8 ml. The organic layer was separated, and the residue was washed with more hot benzene (10 ml). The benzene solutions were combined, dried (MgSO$_4$) and concentrated to afford a brown oil. The oil was purified using 'flash' chromatography and chloroform/methanol 9:1 as eluant. The product fractions were combined and concentrated to afford ethyl 3-[3-cyano-4-(imidazol-1-ylmethyl)phenyl]prop-2-enoate as a brown oil. I.R. (CHCl$_3$ film) $vC=N$: 2230 cm$^{-1}$

EXAMPLE 8

3-[3-Carboxy-4-(imidazol-1-ylmethyl)phenyl]prop-2-enoic acid, hydrochloride hydrate A mixture of ethyl 3-[3-cyano-4-(imidazol-1-ylmethyl)phenyl]prop-2-enoate (0.06 g) in hydrochloric acid (2 ml, 6M) was stirred and boiled for 3 h. The reaction mixture was concentrated under reduced pressure, and toluene (10 ml) was added and the reaction mixture re-concentrated.

Repetition of the toluene/concentration procedure four times gave a solid which was recrystallised from ethanol/ether to afford 3-[3-carboxy-4-(imidazol-1-ylmethyl)phenyl]prop-2-enoic acid hydrochloride hydrate.

EXAMPLE 9

1-[3-(3-Chloro-4-ethoxycarbonylphenyl)prop-2-enyl]imidazole (a) Ethyl 2-chloro-4-iodobenzoate A mechanically stirred mixture of ethyl 4-amino-2-chlorobenzoate (3.6 g, 18.03 mmol) in concentrated hydrochloric acid (10 ml) and water (10 ml) was cooled to 0°, when a solution of sodium nitrite (1.35 g, 19.57 mmol) in water (10 ml) was added dropwise at 0°–5°. Following the addition, the reaction mixture was stirred at 0° for 0.5 h.

A solution of potassium iodide (3.17 g, 19.1 mmol) in water (10 ml) was then added dropwise at 5°–10° and the reaction mixture was then stirred at 5°–10° for 1 h, set aside for 72 h at ambient temperature, and then stirred and boiled for 0.5 h.

The product was extracted with ether (3×10 ml) and the ether solutions were combined and washed with hydrochloric acid (10 ml, 2M), sodium metabisulphite (2×10 ml saturated solution), and with water (10 ml). The ether solution was dried (MgSO$_4$) and concentrated under reduced pressure to afford a brown oil (5.23 g) which was purified by 'flash' chromatography.

(b) A mixture of ethyl 2-chloro-4-iodobenzoate (0.92 g, 2.96 mmol), triphenylphosphine (0.014 g, 0.0534 mmol), triethylamine (0.58 g, 5.73 mmol), 1-allylimidazole (1.2 g, 11.1 mmol), and palladium acetate (0.007 g) in acetonitrile (0.6 ml) was stirred and heated at 120° for 6 h in a steel bomb. The reaction mixture was cooled and concentrated to give an oily solid. The solid was purified by 'flash' chromatography to give 1-[3-(3-chloro-4-ethoxycarbonylphenyl)prop-2-enyl]imidazole as a white solid.

EXAMPLE 10

1-[3-(4-Carboxy-3-chlorophenyl)prop-2-enyl]imidazole hydrochloride hemihydrate

A mixture of 1-[3-(3-chloro-4-ethoxycarbonylphenyl)prop-2-enyl]imidazole (0.09 g) in hydrochloric acid (3 ml, 6M) was stirred and heated under reflux for 3 h. The reaction mixture was concentrated under reduced pressure, and toluene (10 ml) was added and the reaction mixture re-concentrated. Repetition of the toluene/concentration procedure three times afforded a white solid which was recrystallised from ethyl acetate/ethanol/ether to give 1-[3-(4-carboxy-3-chlorophenyl)prop-2-enyl]imidazole hydrochloride hemihydrate as a white crystalline solid, m.p. 247°–249°.

EXAMPLE 11

3-Chloro-4-(imidazol-1-yl)-N-methylcinnanamide

A solution of ethyl (E)-3-[3-chloro-4-(imidazol-1-ylmethyl)phenyl]prop-2-enoate (0.4 g) in ethanolic methylamine (10 ml, 33%) was stood at ambient temperature for 24 h. The reaction mixture was concentrated and the resulting oil was purified by 'flash' chromatography using chloroform/methanol 9:1 as eluant. The product fractions were pooled and concentrated and the resulting solid was recrystallised from ethanol/ether, to give 3-chloro-4-(imidazol-1-yl)-N-methylcinnamamide, m.p. 161°–163°.

EXAMPLE 12

3-[3-Chloro-4-(imidazol-1-ylmethyl)phenyl]prop-2-enoic acid (a) Ethyl 3-[3-chloro-4-(2,2-bismethoxyethylaminomethyl)phenyl]prop-2-enoate.

A mixture of 2,2-dimethoxyethylamine (0.21 g), ethyl 3-(4-bromomethyl-3-chlorophenyl)prop-2-enoate (0.61 g), triethylamine (0.75 ml) and 4-dimethylaminopyridine (0.03 g) in dichloromethane (5 ml) was stirred at ambient temperature for 72 hours. Water (5 ml) was added, and the organic layer was separated. The aqueous layer was washed with ether (2×10 ml), the organic solutions were combined, dried (MgSO$_4$) and concentrated to afford a brown oil. The oil was purified by 'flash' chromatography using chloroform/methanol 9:1 as eluant.

The product fractions were combined and concentrated, to afford ethyl 3-[3-chloro-4-(2,2-bismethoxyethylaminomethyl)phenyl]prop-2-enoate which was used without further purification.

(b) A mixture of ethyl 3-[3-chloro-4-(2,2-bismethoxyethylaminomethyl)phenyl]prop-2-enoate (0.31 g), potassium thiocyanate (0.097 g) in water (5 ml) and ethanol (5 ml) was treated with concentrated hydrochloric acid (1 drop, 12M), and this mixture was then heated at 100° for 16 h, ethanol (5 ml) and water (5 ml) was added periodically. Ammonia solution (40 ml, S.G. 0.88) was added to the reaction mixture, and the mixture was concentrated under reduced pressure. Acetone (100 ml) was added, and the mixture was stirred for 0.25 h and then filtered. The filtrate was concentrated, to give a gum which was purified by 'flash' chromatography, to afford ethyl 3-[3-chloro-4-(2-thioimidazol-1-ylmethyl)phenyl]prop-2-enoate which was used without further purification.

(c) A mixture of ethyl 3-[3-chloro-4-(2-thioimidazol-1-ylmethyl)phenyl]prop-2-enoate (0.05 g) in water (10 ml) and ethanol (10 ml) was treated with ammonia solution (2 ml, S.G. 0.88) and Raney Nickel (≃0.5 g, W2). The reaction mixture was stirred and heated under reflux for 2 h and was then filtered. The residue was washed with hot ethanol, and the combined filtrates were concentrated under reduced pressure to afford a gum. Trituration of the gum with ethanol give a solid which was recrystallised from ethanol/petrol to give ethyl 3-[3-chloro-4-(imidazol-1-ylmethyl)phenyl]prop-2-enoate m.p. 111°–113°.

EXAMPLE 13

3-[3-chloro-4-(imidazol-1-ylmethyl)phenyl]prop-2-enoic acid

A mixture of ethyl 3-[3-chloro-4-(imidazol-1-ylmethyl)phenyl]prop-2-enoate (0.5 g) and sodium hydroxide (0.25 g) in water (10 ml) was stirred and heated under reflux for 3 h. The resulting solution of the sodium salt of the acid was acidified to pH 6 with glacial acetic acid, and the mixture was evaporated to dryness. Ethanol (10 ml) was added to the residue, and the mixture was boiled and filtered. Concentration of the filtrate gave a residue which was recrystallised from ethanol/ether, to give 3-[3-chloro-4-(imidazol-1-ylmethyl)phenyl]prop-2-enoic acid, m.p. 227°–229°.

FORMULATION EXAMPLES

Example A—Tablet formulation

| | |
|---|---|
| Imidazole of formula (I) as a solid or a solid salt thereof | 150 mg |
| Starch | 25 mg |
| Polyvinylpyrrolidone | 2 mg |
| Magnesium stearate | 3 mg |

The imidazole or salt is ground to a fine powder, blended with the starch and then the mixture granulated with an aqueous solution of the polyvinylpyrrolidone. The granules are sieved 1000μ, dried, sieved again and the magnesium stearate added. The mixture is then compressed into tablets.

Example B—Tablet formulation

Tablets (150 mg) of the imidazoles or salts described in the preceding Example are prepared as in the same manner from the following ingredients:

| | |
|---|---|
| The Imidazole Compound (as such or as a salt) | 150 mg |
| Lactose | 100 mg |
| Starch | 30 mg |
| Polyvinylpyrrolidone | 2 mg |
| Magnesium Stearate | 3 mg |

Example C—Tablet formulation

Tablets (100 mg) of the imidazole or salts of Example A are prepared in the same manner from the following ingredients:

| | |
|---|---|
| The Imidazole Compound (as such or as a salt) | 100 mg |
| Sodium starch glycollate | 10 mg |
| Polyvinylpyrrolidone | 2 mg |
| Magnesium stearate | 3 mg |

Example D—Tablet formulation

Tablets (150 mg) of the imidazole or salts of Example A are prepared in the same manner from the following ingredients, except that the starch, pregelled starch and imidazole compound are all blended together prior to granulation:

| | |
|---|---|
| The Imidazole Compound (as such or as a salt) | 150 mg |
| Starch | 25 mg |
| Pregelled starch | 5 mg |
| Magnesium stearate | 3 mg |

Example E—Injectable formulation

| | |
|---|---|
| Imidazole compound (or salt) of formula (I) | 15.0 g |
| Lactic Acid B.P. | q.s. to pH 3.0 |
| Water for Injections B.P. | to 100.0 ml |

Suspend the compound in ¾ of the available quantity of water. Added sufficient lactic acid to dissolve the compound and to reduce the pH to 3.0. Dilute to volume with water for injections.

Sterilise the solution by passage through a membrane filter, pore size 0.22 μm.

Distribute the solution using aseptic precautions into sterilised ampoules, 1 ml per ampoule. Seal by fusion of the glass.

Each 1 ml ampoule supplies 150 mg of the imidazole compound.

Example F—Injectable formulation

| Imidazole compound or salt of formula (I) | 15.0 g |
|---|---|
| Citric Acid B.P. | q.s. to pH 3.0 |
| Chlorocresol | 0.1 g |
| Water for Injections to | 100.0 ml |

Suspended the compound in ½ the final volume of Water for Injections. Add sufficient citric acid as a 10% solution in Water for Injections to dissolve the compound and reduce the pH to 3.0. Dilute to volume with Water for Injection. Sterilise the solution by passage through a membrane filter, pore size 0.22 μm.

Distribute the solution with aseptic precautions into sterilised vials; 25 ml per vial. Stopper with sterile rubber closures and seal with an aluminium cap.

Each 1 ml of solution provides 150 mg of the compound.

Determination of Thromboxane $A_2$ Synthetase Inhibitory Activity

The active compound was dissolved in a suitable solvent at a concentration of 5 mg/ml, and 20 μl added to 0.8 ml of 100 mM Tris buffer (pH 7.5).

The platelets from 5 ml of horse PRP were centrifuged and resuspended in 100 μl of Tris buffer. After lysis by sonication or freeze thawing, the platelet suspension was added to the solution of active compound and equilibrated for 5 min at room temperature. Then 300 ng (50 nCi) of [1-$^{14}$C]-arachidonic acid, dissolved in 100 μl Tris buffer, was added and the mixture incubated for 3 min at 37° C.

The reaction was stopped with 50 μl 2N HCl and the product extracted with 1.5 volumes ethyl acetate by whirling for 30 seconds. 1 ml saturated NaCl was added to the aqueous phase to prevent emulsion formation. The organic layer was removed, dried under $N_2$ and the products redissolved in 50 μl chloroform/methanol mixture for quantitative spotting onto a TLC plate, and subsequent analysis.

The plate was developed in chloroform, methanol, acetic acid, water (90:8:1:0.8), dried and then visualised by autoradiography for 2–3 days.

After development, the autoradiogram was inspected, if the active compound demonstrated some selective inhibitory activity the radioactive $TXB_2$, $PGD_2$, $PGE_2$ and $PGF_2$ zones were scraped off and the radioactivity estimated in a scintillation counter.

The concentration of active compound required to reduce the enzyme activity by 50% ($ED_{50}$) was established. The results are shown in Table A.

TABLE A

| Example | $ED_{50}$ (μg/ml) |
|---|---|
| 1 | 6.6 |
| 2 | 0.5 |
| 3 | 0.05 |
| 4 | 0.08 |
| 6 | 0.015 |
| 10 | 0.35 |

Duration of Action of Thromboxane $A_2$ Synthetase Inhibitors in vivo

N.Z. male rabbits weighing 2.5 kg are anaesthetized with sodium pentobarbitone and chloralose and one carotoid artery is cannulated. Blood samples (1 ml) are taken for incubation; two as controls and one, adding 10 μg indomethacin, as a blank. After each sample is taken the cannula is flushed with saline.

The active compound is then administered orally and further samples at half hour intervals for five to eight hours.

The blood samples for the controls and the active compound are incubated in glass tubes for 45 minutes at 37° C. to clot the blood. Indomethacin is added and the tubes centrifuged to separate the serum which is pipetted off for RIA analysis to determine the concentration of thromboxane $A_2$.

The period of time over which the inhibitor depressed the concentration of thromboxane $A_2$ relative to the controls is then determined.

In this test the compound of Example 1 in a dose of 160 mg/kg was found to have a duration of action of at least 5 hours, while the compound of Example 3 had a duration of action of at least 7 hours at a dose of 2 mg/kg.

We claim:

1. Compounds of the general formula

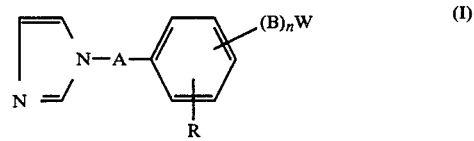

wherein
R is $(Hal)_m$ wherein Hal represents a halogen atom and m is 1 or 2,
W represents a carboxyl or esterified carboxyl,
n is 1, A represents a straight chain or branched $C_{1-3}$ alkylene group, B represents a $C_{2-3}$ alkenylene group and physiologically acceptable salts thereof.

2. Compounds as claimed in claim 1 wherein R is $(Hal)_m$ in which m is 1 and Hal represents a chlorine or bromine atom in the 2-position of the phenyl ring.

3. Compounds as claimed in claim 1 or claim 2 wherein A represents a methylene, ethylene or trimethylene group.

4. Compounds as claimed in claim 1 wherein the —$(B)_n$W substituent is in the 4-position of the phenyl ring.

5. Compounds as claimed in claim 4 wherein n is 1 and B is a group of formula —CH=CH.

6. Compounds as claimed in claim 1 wherein W represents a carboxyl group.

7. Compounds as claimed in claim 1 in the form of their physiologically acceptable acid addition salts.

8. 3-[3-chloro-4-(imidazole-1-ylmethyl)phenyl]-prop-2-enoic acid or a physiologically acceptable salt thereof.

9. 3-[3-Bromo-4-(imidazol-1-ylmethyl)phenyl]-prop-2-enoic acid and its physiologically acceptable salts.

10. (E)-3-[3-chloro-4-(imidazol-1-ylmethyl)phenyl]-prop-2-enoic or a physiologically acceptable salt thereof.

11. Pharmaceutical formulations comprising as active ingredient, at least one compound of formula (I) (as defined in claim 1) or a physiologically acceptable salt thereof, together with at least one pharmaceutical carrier or excipient.

12. A method for the treatment or prophylaxis of thrombo-embolic disorders in a mammal which comprises administering to the mammal an effective amount of a compound of formula (I) (as defined in claim 1) or a physiologically effective salt thereof.

13. A method as claimed in claim 12 wherein the mammal is man.

14. A pharmaceutical formulation comprising the compound or salt of claim 8 together with at least one pharmaceutical carrier or excipiant.

15. A method for the treatment of a thrombo-ambolic disorder in a mammal having such disorder comprising the administration to said mammal of an effective treatment amount of the compound or salt of claim 8.

16. The method of claim 15 in which the mammal is man.

17. The hydrochloride salt of (E)-3-[3-chloro-4-(imidazol-1-ylmethyl)phenyl]prop-2-enoic acid.

18. A method of inhibiting thromboxane $A_2$ synthatase in a human in need thereof which comprises administering to said human an effective thromboxane $A_2$ synthatase inhibitory amount of (E)-3-[3-chloro-4-(imidazol-1-ylmethyl)phenyl]prop-2-enoic acid or a physiologically acceptable salt thereof.

19. The method of claim 18 in which hydrochloride salt is administered.

* * * * *